Figure 1:
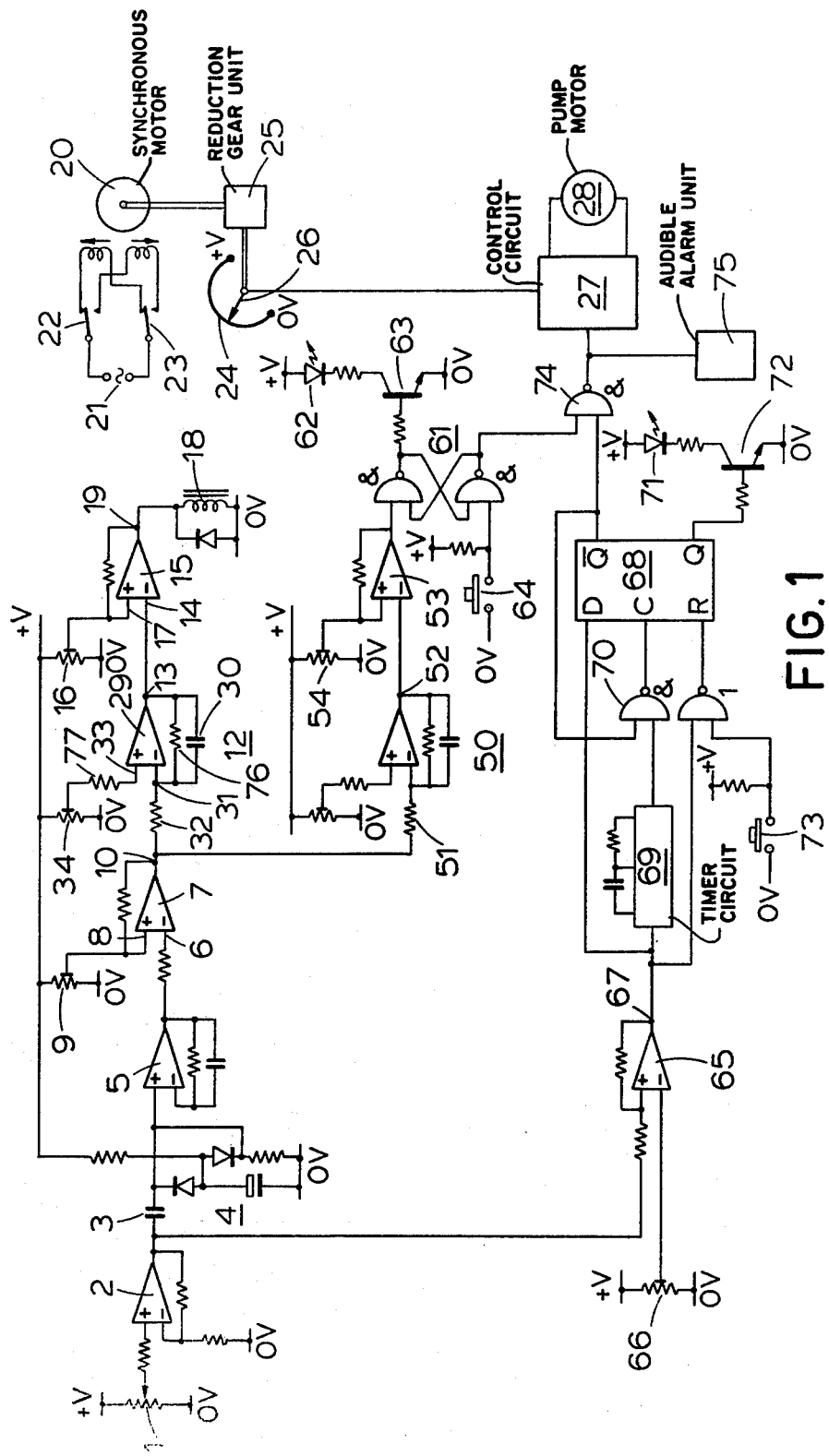

United States Patent [19]

Ellson

[11] 4,213,455
[45] Jul. 22, 1980

[54] APPARATUS FOR THE INFUSION OF A LABOR-INDUCING DRUG INTO THE BLOODSTREAM OF A PATIENT

[75] Inventor: Allan H. Ellson, Harpenden, England

[73] Assignee: Pye (Electronic Products) Ltd., Cambridge, England

[21] Appl. No.: 921,727

[22] Filed: Jul. 3, 1978

[30] Foreign Application Priority Data

Jul. 5, 1977 [GB] United Kingdom ............... 28058/77
Dec. 2, 1977 [GB] United Kingdom ............... 28058/77

[51] Int. Cl.² ............................................. A61M 5/16
[52] U.S. Cl. ................................................. 128/214 E
[58] Field of Search .................. 128/213, 214 E, 260, 128/778

[56] References Cited

U.S. PATENT DOCUMENTS

| | | | |
|---|---|---|---|
| 3,450,153 | 6/1969 | Hildebrant et al. | 128/214 E |
| 3,599,628 | 8/1971 | Abbenante et al. | 128/778 |
| 3,871,361 | 3/1975 | Kamen | 128/214 E |
| 4,078,562 | 3/1978 | Friedman | 128/213 |

Primary Examiner—William E. Kamm
Attorney, Agent, or Firm—Thomas A. Briody; William J. Streeter; Bernard Franzblau

[57] ABSTRACT

Apparatus for controlling the infusion rate of a labor-inducing drug as a function of the rate of uterine contraction includes means for producing a constant amplitude pulse train with the pulse duration determined by the duration of uterine contraction. The pulse train is integrated to produce a signal by means of which the infusion rate can be controlled automatically.

23 Claims, 2 Drawing Figures

APPARATUS FOR THE INFUSION OF A LABOR-INDUCING DRUG INTO THE BLOODSTREAM OF A PATIENT

The present invention relates to apparatus for the infusion of a labour-inducing drug into the bloodstream of a patient during childbirth.

Labour may be artificially induced by use of the synthetic hormone oxytocin. It is necessary to administer oxytocin continuously throughout most of the period of labour. The usual procedure is to make up the oxytocin in a solution of known strength and to infuse the solution into the patient's bloodstream at a rate such as to provide the desired oxytocin dose (infusion) rate.

One problem is to determine the correct dose (infusion) rate since it is found that the requirement varies widely between individuals and also during the perod of each labour. In general the dose (infusion) rate necessary to maintain satisfactory progress of labour will lie in the range of 1 to 128 milliunits of oxytocin per minute, with some 80% of cases lying in the range of 4 to 32 milliunits per minute.

If the dose rate is too low, the uterus does not contract strongly enough to cause labour to progress, but if the dose rate is too high, the uterus may contract too strongly and/or too frequently. This may result in maternal or foetal distress. It was found to be desirable to commence the infusion at a low dose rate and to increase this rate gradually during a period of time until labour was established.

In known apparatus for the infusion of oxytocin, the dose rate is controlled by varying the output of an infusion pump which is arranged to deliver oxytocin solution of known concentration (typically 10 units oxytocin in 500 ml. of 5% dextrose solution) to a cannula inserted into a vein of the patient. The pump, of the positive displacement peristaltic type, is driven by an electric motor provided with a control circuit such that the rotational speed of the motor, and hence the speed of the pump, is determined by the value of a d.c. reference potential applied to the control circuit. The control circuit may comprise a servo system in which a feedback signal representative of the actual speed of the motor is compared with the reference signal, and the motor drive current controlled to minimise any difference. The feedback signal may be derived from the back-EMF of a d.c. motor or from a tacho-generator coupled to the motor output shaft. In an alternative arrangement the pump is driven by a stepping motor which is itself driven by a train of pulses derived from the output of a voltage-controlled oscillator whose frequency is determined by the value of the reference potential.

Since the output per revolution of the pump is substantially constant, the dose rate is directly proportional to the pump speed, and hence to the value of the reference potential.

The reference potential is obtained from the slider of a reference potentiometer connected across a stabilised d.c. supply. A constant-speed motor, known hereinafter as the dose rate motor, is arranged to drive the potentiometer shaft through reduction gearing. Before commencing an infusion the reference potentiometer is set to produce a minimum dose rate, eg. 1 mU oxytocin per minute. At the start of the infusion the dose rate motor is switched on and drives the reference potentiometer so as to increase the dose rate as the infusion proceeds.

The arrangement is such that, in the absence of command signals from a control system to be described hereinafter, the dose rate is doubled approximately every fifteen minutes until the rate of 32 mU oxytocin per minute is reached, whereupon the dose rate motor is automatically switched off and the dose rate thereafter remains constant.

The control system used hertofore is based on the assumption that when labour has been induced and is progressing normally, uterine contractions occur every 2 to 2½ minutes, that the usual duration of a contraction lies in the range of 30 to 60 seconds, that the intra-uterine pressure developed during a normal contraction lies in the range of 30 to 60 mm Hg. and that the resting pressure between contractions lies in the range of 5 to 15 mm Hg.

Intra-uterine pressure is measured by a transducer coupled to the patient by means of a fluid-filled catheter whose open end is inserted into the amniotic fluid. The electrical signal from the transducer is fed via a stabilised buffer amplifier to a first input of a comparator circuit which has applied to a second input a potential corresponding to a pressure of 35 mm Hg. The comparator thus produces an output signal during a contraction in which the intra-uterine pressure equals or exceeds 35 mm Hg. This signal is used to trigger a delay circuit (timer) having a delay period of 2½ minutes. The timer, when triggered, switches off the dose rate motor for the duration of its delay period.

After the start of an infusion, therefore, the dose rate motor runs to increase the dose rate from its initial, low value until a first contraction occurs. The motor is then switched off and the dose rate held constant for 2½ minutes. If no further contraction has occurred in that period, the timer then resets, the dose rate motor is switched on again and the dose rate further increased, until a second contraction is detected, when the timer is again triggered and the motor switched off or a further 2½ minutes.

It will be seen that as the interval between successive contractions decreases, the more frequently is the dose rate motor switched off and the more slowly the dose rate increased, until contractions are occurring at intervals of 2½ minutes or less. The delay timer cannot then reset, the motor is held continuously in the off condition and the dose rate is held constant.

The control circuit also includes means for initiating an alarm and stopping the infusion if abnormal conditions, i.e. spasm or excessive intra-uterine pressure, should occur. Spasm is the condition in which a contraction occurs but is not followed by a relaxation after the normal interval. This condition interferes with the supply of blood to the foetus and may cause foetal anoxia.

To detect spasm, the leading edge of an output signal from the above mentioned comparator is used to trigger a second timer having a period of, e.g. two minutes. If the duration of the output signal exceeds the period of the second timer, a signal is generated which triggers an alarm circuit. This latter circuit, when triggered, produces an audible and/or visual signal to call medical assistance to the patient and also switches off the pump motor of the infusion apparatus, so stopping the supply of oxytocin to the patient.

It is considered that a normal contraction should not result in sustained pressure greater than 80 mm Hg. The output signal from a pressure transducer buffer amplifier is applied to a second comparator circuit which also has applied to it a potential corresponding to a pressure of 80 mm Hg. Any output signal from the second comparator is used to trigger a third timer circuit having a delay period of 10 seconds. Only if the duration of the output signal exceeds the delay of the third timer is a signal generated which is effective to trigger the alarm circuit described above. The 10 second delay prevents alarm condition warnings being given as a result of transient high pressure signals caused by the patients exertions in e.g. changing position, coughing and sneezing.

Although automatic infusion apparatus of the general type described hereinbefore is widely used for the induction of labour, it is found to have certain shortcomings. There is necessarily some delay before the effect on the patient of a particular dose rate of oxytocin becomes apparent. Since in this apparatus the dose rate is progressively increased until a particular level of contraction activity is detected, and thereafter held constant, there is a tendency for the constant rate to be somewhat higher than is necessary to maintain that level of activity. Moreover, it is found with most patients that induction of labour by the administration of oxytocin stimulates the production of natural hormones having a similar effect. In such cases, once labour is established it may be necessary to reduce the oxytocin dose rate rather than to maintain it constant in order to avoid excessive contraction activity with the attendant risk of injury to the baby.

It is an object of the present invention to provide, in apparatus for the infusion of labour inducing drugs, improved means for controlling the dose rate so as to minimise the risk of over-stimulation of labour.

An inevitable feature of the labour process is that the blood supply to the placenta is cut off, or at least tends to be restricted during each contraction. In normal, unassisted labour, this cyclic restriction of the blood supply occurs for no more than about 25% of the total time, that is, on average, a contraction is followed by a rest period lasting at least three times as long. It therefore appears that if, in induced labour, the oxytocin dose rate begins to be reduced as soon as contractions are occurring at a somewhat smaller proportion of the total time, say 20%, there will be no greater risk of foetal anoxia and consequent distress than in normal labour.

According to the present invention, apparatus for the automatic infusion of labour inducing drugs includes a dose rate control system comprising means for producing a pulse train wherein each successive pulse corresponds to a contraction of the patient's uterus and wherein the duration of each pulse is representative of the duration of the corresponding contraction, means for generating a first signal representative of the average value of the mark-space ratio of the pulse train and means responsive to the first signal for deriving a second signal for increasing the dose rate when the said average value is less than a first predetermined value and for reducing the dose rate when the average value exceeds the said first predetermined value.

A control system according to the invention may further comprise means for terminating the infusion when the said average value exceeds a second predetermined value greater than the aforesaid first predetermined value.

Figure 2:
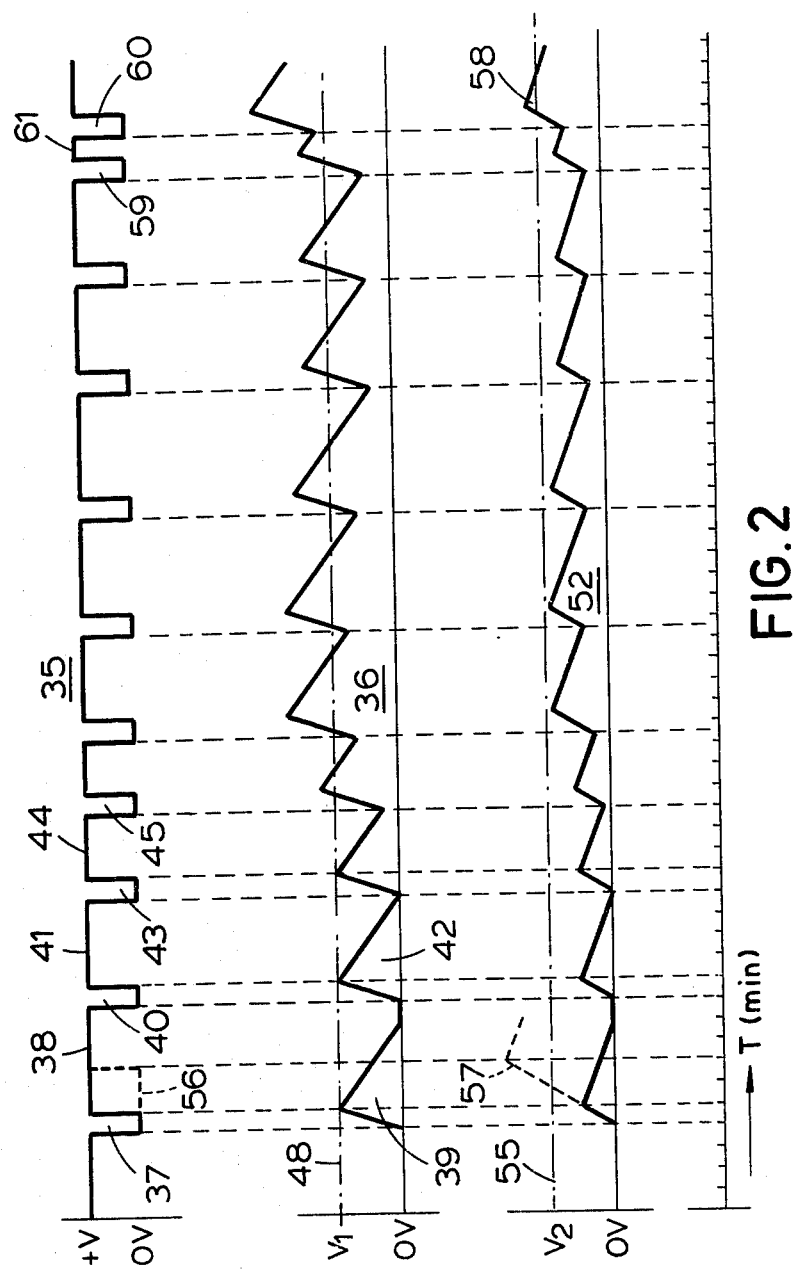

In order that the invention and the manner in which it is to be performed may be clearly understood, an embodiment thereof will be described, by way of example, with reference to the attached drawings, of which FIG. 1 is a schematic circuit diagram of a control system according to the invention, and FIG. 2 illustrates waveforms at particular points in the circuit of FIG. 1.

For the purpose of the following description it is assumed that the placental blood supply will be restricted by intra-uterine pressures in excess of 15 mm Hg and that on average the supply should not be restricted for more than 20% of the total time.

Referring first to FIG. 1, a pressure transducer adapted to produce an electric signal representative of pressures in the range of 0 to 100 mm Hg is indicated symbolically at 1. The transducer is connected to a patient by means of a fluid-filled catheter, not shown in the drawings, whose open end is immersed in the patient's amniotic fluid. The output signal from the transducer 1 is applied to a feedback-stabilised buffer amplifier 2 whose output is connected via a capacitor 3 and a d.c. restoration circuit 4 to an input of a further buffer amplifier 5. The purpose of the d.c. restoration circuit 4, which has a time constant of the order of 15 minutes, is to remove any apparent fluctuation in the base line of the pressure signals due to changes in hydrostatic height of the uterus with respect to the transducer.

The control signal appearing at the output terminal of the amplifier 5, representative of the patient's intra-uterine pressure, is applied to an inverting input terminal 6 of a comparator amplifier 7. A non-inverting input terminal 8 of the comparator 7 is connected to a slider of a potentiometer 9, itself connected between the positive supply rail (+V) and ground (OV). The potentiometer 9 is set to produce at the terminal 8 a potential representative of a selected pressure, typically 15 mm Hg. The arrangement is such that when the potential at the terminal 6 is less than the potential at the terminal 8, the output terminal 10 of the comparator 7 is at a high potential substantially equal to that of the positive supply rail (+V). When the potential at 6 exceeds that at 8, terminal 10 is at a low potential, substantially equal to ground potential (OV). Consequently, during rest intervals between contractions, when the intrauterine pressure is lower than the selected pressure, the potential at terminal 10 is high. During contractions however, terminal 10 is at low potential.

The comparator output terminal 10 is connected to an integrator circuit indicated generally by the reference 12, whose operation will be described hereinafter. An output terminal 13 of the integrator 12 is connected to an inverting input terminal 14 of a second comparator amplifier 15. A potentiometer 16 connected between the positive supply rail and ground has its slider connected to a non-inverting input terminal 17 of the comparator 15. A relay 18 has its operating coil connected between an output terminal 19 of the comparator 15 and ground. The arrangement is such that the relay 18 is energised when the potential at the terminal 14 is less than that at the terminal 17, but is de-energised when the terminal 14 is more positive than the terminal 17.

A synchronous motor 20 of the type having two stator windings has one or the other of its two windings connected to an a.c. supply 21 via change-over contacts 22 and 23 of the relay 18. When the relay 18 is energised, the motor 20 drives in a first, forward direction. When relay 18 is de-energised the motor drives in the reverse direction.

A dose rate potentiometer 24, connected between the positive supply rail and ground, has its slider 26 driven by the motor 20 through a reduction gear unit 25 so that the potential appearing at the slider 26 increases with time when the relay 18 is energised and the motor rotates in the forward direction, and reduces when the relay 18 is de-energised and the motor rotates in reverse. The foregoing elements operate together to derive an infusion rate signal at the slider 26 of potentiometer 24. The slider 26 is connected to an input terminal of a control circuit 27 which is effective to control the speed of a pump motor 28. The motor 28 drives a peristaltic pump, not shown in the drawing, for delivering oxytocin solution to a cannula inserted into a vein of the patient. The control circuit 27, motor 28 and peristaltic pump are well-known in themselves and need not be further described herein.

Before commencing an infusion, the dose rate potentiometer is set to produce a minimum voltage at its slider 26. At the start of the infusion the control circuit 27 causes the motor 28, and with in the peristaltic pump, to operate at a low speed which produces a dose rate of typically one milliunit of oxytocin per minute.

At the start of the infusion, the patient's intra-uterine pressure is at its rest value, i.e. not more than 15 mm Hg. The potential at the inverting input 6 of the comparator 7 is less than that at the non-inverting input 8 so that the output 10 of the comparator 7 remains high. Consequently, the output 13 of the integrator 12 is low, that of the comparator 15 is high, and the relay 18 is energised. The motor 20 therefore commences to drive the dose rate potentiometer in a forward direction, increasing the potential applied to the input of the control unit 27 and increasing the dose rate. The law of the potentiometer 24 and the ratio of the gear unit 25 are chosen so that the dose rate is doubled in each successive period of, typically, 25 minutes.

This situation persists until the dose rate has been increased sufficiently to cause contraction to commence. When a first contraction occurs, the patient's intra-uterine pressure exceeds 15 mmHg. The output 10 of the comparator 7 therefore goes to ground potential (OV) for the duration of the contraction, and returns to a high potential (+V) at the end of the contraction. The integrator 12 therefore charges during the contraction but commences to discharge again at the end of the contraction.

The integrator 12 comprises an operational amplifier 29 provided with a capacitor 30 and resistor 76 connected in parallel between an output terminal 13 and an inverting terminal 31 of the amplifier 29. The output 10 of the comparator 7 is connected to the terminal 31 via an input resistor 32. A non-inverting input terminal 33 of the amplifier 29 is connected to the slider of a potentiometer 34, itself connected between the positive supply rail and ground, via an input resistor 77.

The net current into the integrator 12 is given by the voltage at the terminal 10 divided by the value of the input resistor 32 minus the voltage at the slider of the potentiometer 34 divided by the value of the input resistor 77. It will be seen that when the terminal 10 is at zero volts, i.e. during a contraction, the output terminal 13 of the integrator 12 charges linearly to a positive potential, and when the terminal 10 returns to +V volts during a subsequent rest period, the output terminal 13 discharges linearly towards zero. The relative rates of charge and discharge are dependent on the setting of the potentiometer 34. This is typically set so that the integrator charges from zero to a potential V in one unit of time and discharges from the potential V to zero in four units of time.

Referring now to FIG. 2, the curve 35 represents the variation with time of the potential at the output terminal 10 of the comparator 7 and the curve 36 represents the corresponding variation of the potential at the output terminal 13 of the integrator 12.

The negative-going pulse 37 of 1 minute duration corresponds to the first contraction after the start of an infusion. As shown at 39 the integrator charges to a potential V1 during the pulse 37 and discharges to zero during the first four minutes of the subsequent rest period 38. It will be appreciated that if the pulse 37 were of shorter or longer duration, the integrator would charge to a lower or higher potential as the case may be, but would discharge to zero in a period four times the duration of the pulse.

A second pulse 40, corresponding to a second contraction, is shown as occurring after a rest period 38 of 5 minutes duration. This is followed by a further rest period 41 of four minutes duration. The integrator charges during the pulse 40, as shown at 42, and discharges to zero immediately before the onset of the next pulse 43. This is followed by a rest period 44, shown as being of three minutes duration, and a further pulse 45. The integrator 12 again charges during pulse 43, but in this case cannot fully discharge during the rest period. Consequently it charges to a potential greater than V1 during the pulse 45.

As described hereinbefore, output of the integrator 12 is compared in the comparator 15 with a threshold potential set by the potentiometer 16. The threshold level may typically be set equal to V1, as shown in FIG. 2 by the broken line 48.

It will be seen that for contractions of one minute duration followed by rest periods of not less than 4 minutes, the integrator output does not exceed the threshold level V1. If, however, the duration of the contractions exceeds 20% of the total time, the integrated voltage accumulates over successive periods so that it exceeds the threshold level V1 for a greater proportion of each successive cycle.

The relay 18 is de-energised reversing the drive to the dose rate potentiometer 24 when and only when the integrator output exceeds the threshold level V1. It follows that from the start of an infusion the dose rate is increased until contractions occur with a duration and frequency such that they occupy say 20% of the total time. Thereafter the dose rate is decreased or increased as may be necessary to assist the uterus to continue contracting for periods averaging about 20% of the total time.

The figures of 1 minute duration for individual contractions and 20% ratio of contraction time to total time are purely exemplary. Other values may be chosen by adjustment of the potentiometers 34 and 16. Furthermore, although the integrator circuit herein is an analog device, the same functions can be performed digitally by using an up-down counter driven by clock pulses gated by the contraction signal.

The control system further comprises means for operating an alarm and for switching off the pump drive motor 28 to terminate the infusion of the drug if any of the three following conditions obtain:
  (i) The uterus continues to contract, on average, for periods substantially greater than 20% of the total time despite a reduction of dose rate.
  (ii) An individual contraction persists for more than two minutes (spasm).

(iii) The intra-uterine pressure exceeds a danger level of (say) 80 mm Hg for 10 seconds or more.

(i) and (ii) above are achieved by providing a further integrator circuit 50 fed supplied with a train of pulses from the output 10 of the comparator 7. The integrator 50 is similar to the integrator 12 described hereinbefore save that its input resistor 51 has a value double that of the resistor 32. The integrator 50 therefore has an integration time constant double that of the integrator 12. For any given width of input pulse, its output is therefore half that of the integrator 12, as shown by the curve 52 in FIG. 2.

The output 52 of the integrator 50 is fed to a comparator 53 which also receives a threshold potential V2 set by a potentiometer 54 and shown in FIG. 2 by the broken line 55. Typically V2 is set equal to V1. The comparator output will remain high until the potential at the output 52 exceeds the threshold level V2, whereupon it will fall to zero.

At 56 in FIG. 2 there is shown in broken outline a pulse at the output 10 of the comparator 7 having a duration of 3 minutes. The corresponding output from the integrator 50 is indicated by the broken line 57. It will be seen that the integrator output exceeds the reference level V2 (=V1) after two minutes, i.e. when spasm occurs.

At 59 and 60 are shown two successive contraction pulses with an intervening rest period 61 substantially shorter than normal. As shown at 58, the output of the integrator 50 exceeds the reference level for this condition.

The output of the comparator 53 is applied to an input of a latch circuit 61 comprising a pair of cross-connected NAND gates. The latch 61 is set when the output of the comparator 53 goes to zero, i.e. when either of the alarm conditions (i) or (ii) above exists. A light emitting diode 62 is energised via a transistor 63 when the latch 61 is set. A push-button switch 64 is provided for resetting the latch 61 after an alarm.

A circuit of known form is employed to provide an alarm in the excess pressure condition (iii) above. Briefly, the output of the buffer amplifier 2 is fed to a non-inverting input of a comparator 65 whose inverting input is supplied with a potential corresponding to an intra-uterine pressure of 80 mm Hg derived from a slider of a preset potentiometer 66 connected between the stabilised positive supply line and ground. The output 67 of the comparator 64 is normally at zero potential and goes positive if and only if the intra-uterine pressure exceeds 80 mm Hg.

The output 67 of the comparator 65 is connected to a D input of a D type flip-flop unit 68 and also to an input of a timer circuit 69 which produces a positive-going output signal having a duration of 10 seconds from the instant at which its input goes positive. The output of the timer 69 is connected to a clock input (C) of the flip-flop 68 via a NAND gate 70. The arrangement is such that the flip-flop 68 is clocked by the back edge of the timer output pulse, i.e. 10 seconds after the output of the comparator 65 went positive. Hence, if the excess pressure has persisted and the D input is still positive when the flip-flop 68 is clocked, the Q output of the flip-flop is set positive.

A light emitting diode 71, driven by a transistor 72 controlled from the Q output, is illuminated when the flip-flop 68 is in the set (alarm) condition. A push button switch 73 permits resetting of the flip-flop 68 after an alarm.

An inverse output of the latch 61 and a $\overline{Q}$ output of the flip-flop 68 are connected to respective inputs of a NAND gate 74. The output of the gate 74 therefore goes positive if either the latch 61 or the flip-flop 68 (or both) is in the set (alarm) condition. The output of the gate 74 is connected to the pump motor control circuit 27 and is effective, when positive, to stop the pump motor 28 and with it the infusion pump, so terminating the infusion if any one or more of the alarm conditions (i) to (iii) above occurs. The output of the gate 74 may be further connected to an audible alarm unit 75.

What we claim is:

1. A control system for controlling the infusion rate of a labor-inducing drug into the bloodstream of a patient comprising, means responsive to a control signal determined by the intra-uterine pressure of the patient for producing a train of pulses wherein each successive pulse corresponds to a contraction of the patient's uterus and wherein the duration of each pulse is representative of the duration of the corresponding contraction, means responsive to the train of pulses for generating a first signal representative of the average value of the mark-space ratio of the pulse train, and means responsive to said first signal for deriving a second signal for increasing the infusion rate when the said average value is less than a first predetermined value and for reducing the infusion rate when the average value exceeds the said first predetermined value.

2. A control system as claimed in claim 1 which further comprises means controlled by said control signal for terminating the infusion of said drug when the said average value exceeds a second predetermined value greater than said first predetermined value.

3. A control system as claimed in claim 1 which further comprises means responsive to said pulse train for terminating the infusion of said drug if the duration of the pulses exceeds a period which is at least 20% of the pulse repetition period of the pulse train.

4. A control system as claimed in claim 2 wherein the terminating means includes means for measuring the duration of each intra-uterine contraction and for terminating the infusion of said drug if any contraction persists for more than a given time period.

5. A control system as claimed in claim 4 wherein the given time period is two minutes.

6. A control system as claimed in claim 1 further comprising means responsive to said control signal for terminating the infusion of said drug if the said pressure exceeds a given level for a predetermined time period.

7. A control system as claimed in claim 6 wherein the given level of said pressure is 80 mm Hg and the predetermined time period is ten seconds.

8. A control system as claimed in claims 1, 2 or 3 wherein the means for generating a first signal comprises an integrator circuit adapted to charge at a first rate during each pulse of the pulse train and to discharge at a second rate during each interval between pulses of the pulse train.

9. A control system as claimed in claim 8 including means for varying the rates of charge and of discharge of the integrator circuit.

10. A control system as claimed in claims 1, 2 or 3 further comprising a pressure transducer for providing said control signal determined by the patient's intra-uterine pressure, and the means for producing the pulse train comprises d.c. restoration means responsive to said control signal to reduce variations in the control signal caused solely by changes in the relative hydrostatic height of the patient and the transducer.

11. A control system as claimed in claims 1, 2 or 3 wherein said second signal deriving means comprises an infusion rate control potentiometer and a motor coupled to drive said potentiometer in direction to increase the infusion rate when the average value of the second signal is less than the said predetermined value and in a direction to reduce the infusion rate when the said average value exceeds the said predetermined value.

12. A control system as claimed in claims 1, 2 or 3 wherein said means for producing a pulse train comprises, a comparator having a first input coupled to receive said control signal and a second input, a source of reference voltage having a value representing a predetermined intra-uterine pressure value and coupled to the second input of the comparator whereby the comparator produces a pulse train of constant amipitude at an output and with each pulse of the pulse train corresponding to an intra-uterine contraction for which the intra-uterine pressure exceeds said predetermined pressure and with the pulse duration being determined by the duration of the contraction.

13. Apparatus for the infusion of a labor-inducing drug into the bloodstream of a patient at an infusion rate controllable as a function of the rate of uterine contraction of the patient comprising, pumping means for infusing the drug at a rate dependent on the value of an infusion rate signal, applied thereto means for measuring the intra-uterine pressure of the patient and producing a control signal determined thereby, and a control system comprising: a comparison device which compares the control signal with a reference signal representing a predetermined intra-uterine pressure value to provide a train of pulses of substantially constant amplitude with each pulse of the pulse train corresponding to a contraction of the patient's uterus for which the measured intra-uterine pressure is greater than the predetermined pressure, the duration of each pulse being representative of the duration of the corresponding contraction, integrating means responsive to said pulse train for generating a signal representative of the average value of the mark-space ratio of the pulse train, and means responsive to said signal for deriving said infusion rate signal which increases in value when said average value is less than a first predetermined value and which decreases in value when the average value is greater than the first predetermined value.

14. Apparatus as claimed in claim 13 wherein the control system further comprises means responsive to said train of pulses for terminating the infusion of said drug if said average value exceeds a second predetermined value greater than the said first predetermined value.

15. Apparatus as claimed in claim 14 wherein the control system further comprises means for terminating the infusion of said drug if the duration of a pulse exceeds a predetermined fraction of the pulse repetition period of the pulse train.

16. Apparatus as claimed in claim 14 wherein the terminating means includes means for measuring the duration of each intra-uterine contraction and for terminating the infusion of said drug if any contraction persists for more than a given time period.

17. Apparatus as claimed in claim 13 further comprising means responsive to said control signal for terminating the infusion of said drug if the said intra-uterine pressure exceeds a given level for a predetermined time period.

18. Apparatus as claimed in claims 13, 14, 15, 16 or 17 wherein the integrating means includes a capacitor which charges at a first rate during each pulse of the pulse train and discharges at a second rate during each interval between pulses of the pulse train.

19. Apparatus as claimed in claim 18 including means for varying the rates of charge and of discharge of the capacitor of the integrating means.

20. Apparatus as claimed in claim 13 wherein the measuring means comprises a pressure transducer for producing said control signal determined by the patient's intra-uterine pressure, and further comprising d.c. restoration means coupled between the pressure transducer and the comparison device and operated to reduce variations in the control signal caused solely by changes in the relative hydrostatic height of the patient and the transducer.

21. Apparatus as claimed in claim 13 wherein said infusion rate signal deriving means includes an infusion rate control potentiometer and a motor coupled to drive said rate control potentiometer in a direction to increase the infusion rate when the average value of the mark-space ratio is less than said first predetermined value and to drive said potentiometer in a direction to reduce the infusion rate when the average value exceeds the first predetermined value.

22. A control system as claimed in claims 2 or 3 wherein said first signal generating means comprises a first integrator circuit including a capacitor which charges at a first rate during each pulse of the pulse train and discharges at a second rate during each interval between pulses of the pulse train, and wherein said terminating means includes a second integrator circuit having a capacitor that charges at a different rate than the capacitor of the first integrator circuit.

23. A control system as claimed in claim 8 wherein said first signal generating means further comprises a comparison device having a first input coupled to an output of said integrator circuit, a second input coupled to a source of reference voltage and an output for deriving said second signal.

* * * * *

UNITED STATES PATENT AND TRADEMARK OFFICE
CERTIFICATE OF CORRECTION

PATENT NO. : 4,213,455

DATED : July 22, 1980

INVENTOR(S) : ALLAN H. ELLSON

It is certified that error appears in the above—identified patent and that said Letters Patent is hereby corrected as shown below:

Column 8, Claim 10, line 2, change "providing" to --producing--

Column 9, Claim 11, line 4, after "in" insert --a--

Column 9, Claim 12, line 8, change "ampitude" to --amplitude--

Column 9, Claim 13, line 6, after "signal" delete ","
after "thereto" insert --,--

Signed and Sealed this

Thirteenth Day of September 1983

[SEAL]

Attest:

GERALD J. MOSSINGHOFF

*Attesting Officer*  *Commissioner of Patents and Trademarks*